United States Patent

Butler et al.

(10) Patent No.: US 7,268,264 B2
(45) Date of Patent: *Sep. 11, 2007

(54) CRITICAL PHASE ALKYLATION PROCESS

(75) Inventors: James R. Butler, Webster, TX (US);
Kevin P. Kelly, Friendswood, TX (US)

(73) Assignee: Fina Technology, Inc., Houston, TX (US)

( * ) Notice: Subject to any disclaimer, the term of this patent is extended or adjusted under 35 U.S.C. 154(b) by 0 days.

This patent is subject to a terminal disclaimer.

(21) Appl. No.: 10/269,639

(22) Filed: Oct. 4, 2002

(65) Prior Publication Data

US 2004/0068152 A1   Apr. 8, 2004

(51) Int. Cl.
*C07C 2/68* (2006.01)
*C07C 15/12* (2006.01)

(52) U.S. Cl. .................. 585/323; 585/475; 585/467

(58) Field of Classification Search ............... 585/467, 585/475, 323
See application file for complete search history.

(56) References Cited

U.S. PATENT DOCUMENTS

| | | | |
|---|---|---|---|
| 3,251,897 A * | 5/1966 | Wise | ............. 585/455 |
| 3,308,069 A | 3/1967 | Wadlinger et al. | |
| 4,185,040 A | 1/1980 | Ward et al. | |
| 4,605,811 A * | 8/1986 | Tiltscher et al. | ............. 585/670 |
| 4,642,226 A | 2/1987 | Calvert et al. | |
| 4,774,379 A | 9/1988 | Butler et al. | |
| 4,891,458 A | 1/1990 | Innes et al. | |
| 5,744,673 A | 4/1998 | Skeels et al. | |

(Continued)

FOREIGN PATENT DOCUMENTS

EP    0159846 A2    10/1985

(Continued)

OTHER PUBLICATIONS

W.M. Meier, D.H. Olson, Atlast of Zeolite Structure Types, 1992, p. 58, Heinemann.

(Continued)

*Primary Examiner*—Thuan Dinh Dang
(74) *Attorney, Agent, or Firm*—William D. Jackson; Shirley A. Kopecky

(57) ABSTRACT

A process for the production of ethylbenzene by the ethylation of benzene in the critical phase over a molecular sieve aromatic alkylation catalyst. An aromatic feedstock having a benzene content of at least 90 wt. % is supplied into a reaction zone into contact with a zeolite beta alkylation catalyst having a silica/alumina ratio within the range of 20-500, specifically 50-150. The alkylation catalyst is a zeolite beta specifically a lanthanum-modified zeolite beta. Ethylene is supplied to the reaction zone to provide a benzene/ethylene mole ratio of 1-15. The reaction zone is operated under conditions in which benzene is in the supercritical phase to produce an alkylation product containing ethylbenzene as a primary product with heavier alkylated by-products of no more than 60 wt. % of the ethylbenzene. The alkylation product is recovered from the reaction zone and supplied to a separation and recovery zone to separate ethylbenzene from a polyalkylated component including diethylbenzene. At least a portion of the polyalkylated component is supplied to a transalkylation reaction zone containing a molecular sieve transalkylation catalyst. The transalkylation reaction zone contains a zeolite Y catalyst and is operated under liquid phase conditions.

21 Claims, 12 Drawing Sheets

U.S. PATENT DOCUMENTS 5,847,255 A * 12/1998 Ghosh et al. ............... 585/467
5,907,073 A    5/1999 Ghosh
6,043,402 A    3/2000 Gajda
6,303,840 B1  10/2001 Poliakoff et al.
6,376,729 B1   4/2002 Merrill et al.

FOREIGN PATENT DOCUMENTS

EP    0186447 A2    7/1986
EP    0507761 A1   10/1992

OTHER PUBLICATIONS

Higgins et al., "The Framework Topology of Zeolite Beta," Zeolites, 1998, Nov. 1998, pp. 446-452, vol. 8.

* cited by examiner

- ◆ pr-benzenes
- ■ bu-benzenes
- ▲ heavies

♦ pr-benzenes
■ bu-benzenes
▲ heavies

- ◆ pr-benzenes
- ■ bu-benzenes
- △ heavies

- ◆ pr-benzenes
- ■ bu-benzenes
- ▲ heavies

CRITICAL PHASE ALKYLATION PROCESS

FIELD OF THE INVENTION

This invention relates to the production of ethylbenzene and more particularly to the ethylation of benzene under the conditions in which the benzene is in the supercritical phase.

BACKGROUND OF THE INVENTION

The alkylation of benzene with ethylene over a molecular sieve catalyst is a well-known procedure for the production of ethylbenzene. Typically, the alkylation reaction is carried out in a multistage reactor involving the interstage injection of ethylene and benzene to produce an output from the reactor that involves a mixture of monoalkyl and polyalkylbenzene. The principal monoalkylbenzene is, of course, the desired ethylbenzene product. Polyalkylbenzenes include diethylbenzene, triethylbenzene, and xylenes.

In many cases, it is desirable to operate the alkylation reactor in conjunction with the operation of a transalkylation reactor in order to produce additional ethylbenzene through the transalkylation reaction of polyethylbenzene with benzene. The alkylation reactor can be connected to the transalkylation reactor in a flow scheme involving one or more intermediate separation stages for the recovery of ethylene, ethylbenzene, and polyethylbenzene.

Transalkylation may also occur in the initial alkylation reactor. In this respect, the injection of ethylene and benzene between stages in the alkylation reactor not only results in additional ethylbenzene production but also promotes transalkylation within the alkylation reactor in which benzene and diethylbenzene react through a disproportionation reaction to produce ethylbenzene.

Various phase conditions may be employed in the alkylation and transalkylation reactors. Typically, the transalkylation reactor will be operated under liquid phase conditions, i.e., conditions in which the benzene and polyethylbenzene are in the liquid phase, and the alkylation reactor is operated under gas phase conditions, i.e., pressure and temperature conditions in which the benzene is in the gas phase. However, liquid phase conditions can be used where it is desired to minimize the yield of undesirable by-products from the alkylation reactor.

SUMMARY OF THE INVENTION

In accordance with the present invention, there is provided a process for the production of ethylbenzene by the ethylation of benzene in the critical phase over a molecular sieve aromatic alkylation catalyst. In one aspect of the invention, an aromatic feedstock having a benzene content of at least 90 wt. % is supplied into a reaction zone and into contact with a zeolite beta alkylation catalyst. The zeolite beta preferably has a silica-alumina ratio within the range of 20-500 and more preferably within the range of 50-150. Ethylene is supplied to the alkylation reaction zone in an amount to provide a benzene/ethylene mole ratio of 1-15 and preferably with the range of 3-8. The reaction zone is operated at temperature and pressure conditions in which benzene is in the super critical phase to cause of ethylation of the benzene in the presence of the zeolite beta alkylation catalyst. An alkylation product is produced containing ethylbenzene as a primary product with the attendant production of heavier alkylated by-products of no more than 60 wt. % of the ethylbenzene. The alkylation product is recovered from the reaction zone for further use or processing.

In a further aspect of the invention, there is provided a process for the production of ethylbenzene in a critical phase alkylation reaction zone followed by the transalkylation of a polyalkylated aromatic component. In this aspect of the invention, there is provided an alkylation reaction zone containing a molecular sieve aromatic alkylation catalyst. A feedstock containing benzene in an amount of at least 95 wt. % of the aromatic content of the feedstock as a major component and ethylene as a minor component is supplied to the alkylation reaction zone. The alkylation reaction zone is operated at temperature and pressure conditions at which benzene is in the super critical phase to cause ethylation of the benzene in the presence of the molecular sieve alkylation catalys and to produce an alkylation product comprising a mixture of benzene, ethylbenzene, and polyalkylated aromatics, including diethylbenzene. The alkylation product is recovered from the alkylation reaction zone and supplied to a separation and recovery zone. In the recovery zone, ethylbenzene is separated and recovered from the product as well as the separation of a polyalkylated component including diethylbenzene. At least a portion of the polyalkylated aromatic component, including diethylbenzene, is supplied to a transalkylation reaction zone containing a molecular sieve transalkylation catalyst. Benzene is also supplied to the transalkylation reaction zone, and the transalkylation reaction zone is operated under temperature and pressure conditions to cause disproportionation of the polyalkylated aromatic fraction to produce a disproportionation product having a reduced diethylbenzene content and an enhanced ethylbenzene content. Preferably, the transalkylation reaction zone contains a zeolite Y catalyst and is operated under conditions to maintain the polyalkylated aromatic component in the liquid phase. Preferably, the alkylation catalyst is a zeolite beta, preferably a rare earth-modified zeolite beta. A specific zeolite beta is a lanthanum-modified zeolite beta.

DETAILED DESCRIPTION OF THE INVENTION

Figure 1:
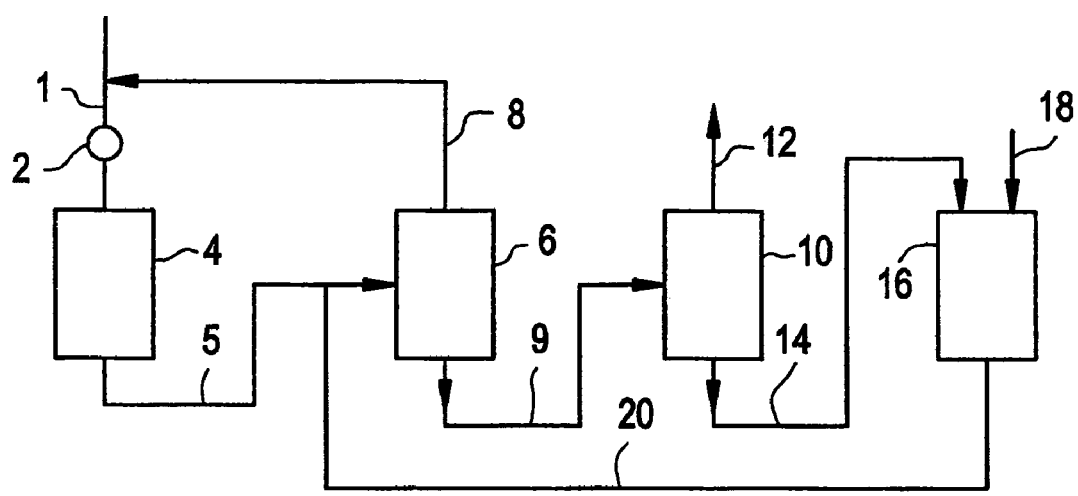
FIG. 1 is an idealized schematic block diagram of an alkylation/transalkylation process embodying the present invention.

The present invention involves the critical phase alkylation of benzene over a molecular sieve alkylation catalyst under conditions to control and desirably minimize the yield of by-products in the alkylation reaction zone. The feedstock supplied to the alkylation reaction zone comprises benzene as a major component and ethylene as a minor component. Typically, the benzene and ethylene streams will be combined to provide a benzene-ethylene mixture into the reaction zone. The benzene stream, which is mixed with the ethylene either before or after introduction into the reaction zone, should be a relatively pure stream containing only very small amounts of contaminants. The benzene stream should contain at least 95 wt. % benzene. Preferably, the benzene stream will be at least 98 wt. % benzene with only trace amounts of such materials as toluene, ethyl benzone, and $C_7$ aliphatic compounds that cannot readily be separated from benzene. The alkylation reaction zone is operated under supercritical conditions, that is, pressure and temperature conditions which are above the critical pressure and critical temperature of benzene. Specifically, the temperature in the alkylation zone is at or above 310° C., and the pressure is at or above 550, psia preferably at least 600 psia. Preferably, the temperature in the alkylation reactor will be maintained at an average value within the range of 320-350° C. and a pressure within the range of 550-1600 psia and more preferably 600-800 psia. The critical phase alkylation reaction is exothermic with a positive temperature gradient from the inlet to the outlet of the reactor, typically providing a temperature increment increase within the range of about 20-40° C.

The operation of the alkylation reaction zone in the supercritical region enables the alkylation zone to be operated under conditions in which the benzene-ethylene mole ratio can be maintained at relatively low levels, usually somewhat lower than the benzene-ethylene mole ratio encountered when the alkylation reaction zone is operated under liquid phase conditions. In most cases, the benzene-ethylene mole ratio will be within the range of 1-15. Preferably, the benzene/ethylene mole ratio will be maintained during at least part of a cycle of operation at a level within the lower end of this range, specifically, at a benzene-ethylene mole ratio of less than 10. Thus, operation in the supercritical phase offers the advantages of gas phase alkylation in which the benzene-ethylene ratio can be kept low but without the problems associated with by-product formation, specifically xylene formation, often encountered in gas-phase alkylation. At the same time, operation in the super critical phase offers the advantages accruing to liquid phase alkylation in which the by-product yield is controlled to low levels. The pressures required for operation in the super critical phase are not substantially greater than those required in liquid phase alkylation, and the benzene in the supercritical phase functions as a solvent to keep the molecular sieve catalyst clean and to retard coking leading to deactivation of the catalyst.

Turning now to FIG. 1, there is illustrated a schematic block diagram of an alkylation/transalkylation process employing the present invention. As shown in FIG. 1, a product stream comprising a mixture of ethylene and benzene in a mole ratio of benzene to ethylene about 1 to 15 is supplied via line 1 through a heat exchanger 2 to an alkylation reaction zone. Alkylation zone 4 preferably comprises one or more multi-stage reactors having a plurality of series-connected catalyst beds containing a molecular sieve alkylation catalyst as described herein. The alkylation zone 4 is operated at temperature and pressure conditions to maintain the alkylation reaction in the supercritical phase, i.e. the benzene is in the supercritical state, and at a feed rate to provide a space velocity enhancing diethylbenzene production while retarding by-products production. Preferably, the space velocity of the benzene feed stream will be within the range of 10-150 hrs$^{-1}$ LHSV per bed, and more specifically 40-100 hrs$^{-1}$ LHSV per bed.

The output from the alkylation reactor 4 is supplied via line 5 to an intermediate benzene separation zone 6 that may take the form of one or more distillation columns. Benzene is recovered through line 8 and recycled through line 1 to the alkylation reactor. The bottoms fraction from the benzene separation zone 6, which includes ethylbenzene and polyalkylated benzenes including polyethylbenzene and xylene, is supplied via line 9 to an ethylbenzene separation zone 10. The ethylbenzene separation zone may likewise comprise one or more sequentially connected distillation columns. The ethylbenzene is recovered through line 12 and applied for any suitable purpose, such as in the production of vinyl benzene. The bottoms fraction from the ethylbenzene separation zone 10, which comprises polyethylbenzene, principally diethylbenzene, is supplied via line 14 to a transalkylation reactor 16. Benzene is supplied to the transalkylation reaction zone through line 18. The transalkylation reactor, which preferably is operated under liquid phase conditions, contains a molecular sieve catalyst, preferably zeolite-Y, which has a somewhat larger pore size than the molecular sieve used in the alkylation reaction zone. The output from the transalkylation reaction zone is recycled via line 20 to the benzene separation zone 6.

Figure 2:
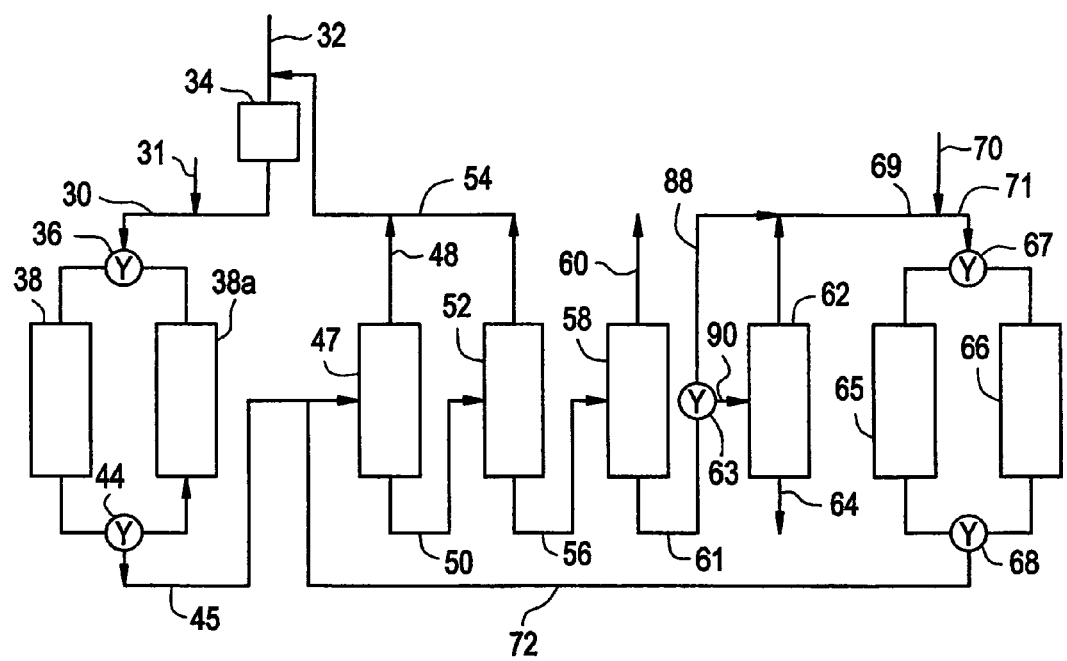
FIG. 2 is a schematic illustration of a preferred embodiment of the invention incorporating separate parallel-connected alkylation and transalkylation reactors with an intermediate multi-stage recovery zone for the separation and recycling of components.

Referring now to FIG. 2, there is illustrated in greater detail a suitable system incorporating a multi-stage intermediate recovery zone for the separation and recycling of components involved in the critical phase alkylation and transalkylation process. As shown in FIG. 2, an input feed stream is supplied by fresh ethylene through line 31 and fresh benzene through line 32. As noted previously, the fresh benzene stream, supplied via line 32, is of high purity containing at least 98 wt. %, preferably about 99 wt. % benzene with no more than 1 wt. % other components. Typically, the fresh benzene stream will contain about 99.5 wt. % benzene, less than 0.5% ethylbenzene, with only trace amounts of non-aromatics and toluene. Line 32 is provided with a preheater 34 to heat the benzene stream consisting of fresh and recycled benzene to the desired temperature for the supercritical alkylation reaction. The feed stream is supplied through a two-way, three-position valve 36 and inlet line 30 to the top of one or both parallel critical phase alkylation reactor 38 and 38A comprising a plurality of series connected catalyst beds each of which contains the desired molecular sieve alkylation catalyst. The reactors are operated at an average temperature, preferably within the range of 310°-350° C. inlet temperature and at pressure conditions of about 550 to 800 psia, to maintain the benzene in the critical phase.

In normal operation of the system depicted in FIG. 2, both reaction zones 38 and 38A may, during most of a cycle of operation, be operated in a parallel mode of operation in which they are both in service at the same time. In this case, valve 36 is configured so that the input stream in line 30 is roughly split in two to provide flow to both reactors in-approximately equal amounts. Periodically, one reactor can be taken off-stream for regeneration of the catalyst. Valve 36 is then configured so that all of the feed stream from line 30 can be supplied to reactor 38 while the catalyst beds in reactor 38A are regenerated and visa versa. The regeneration procedure will be described in detail below but normally will take place over a relatively short period of time relative to the operation of the reactor in parallel alkylation mode. When regeneration of the catalyst beds in reactor 38A is completed, this catalyst can then be returned on-stream, and at an appropriate point, the reactor 38 can be taken off-stream for regeneration. This mode of operation involves operation of the individual reactors at relatively lower space velocities for prolonged periods of time with periodic relatively short periods of operation at enhanced, relatively higher space velocities when one reactor is taken off-stream. By way of example, during normal operation of the system with both reactors 38 and 38A on-stream, the feed stream is supplied to each reactor to provide a space velocity of about 25-45 hrs.$^{-1}$ LHSV. When reactor 38A is taken off-stream and the feed rate continues unabated, the space velocity for reactor 38 will approximately double to 50-90 hr.$^{-1}$ LHSV. When the regeneration of reactor 38A is completed, it is placed back on-stream, and again the feed stream rate space velocity for each reactor will decrease to 25-45 hr.$^{-1}$ until such point as reactor 38 is taken off-stream, in which case the flow rate to reactor 38A will, of course, increase, resulting again in a transient space velocity in reactor 38 of about 50-90 hr$^{-1}$ LHSV.

Figure 3:
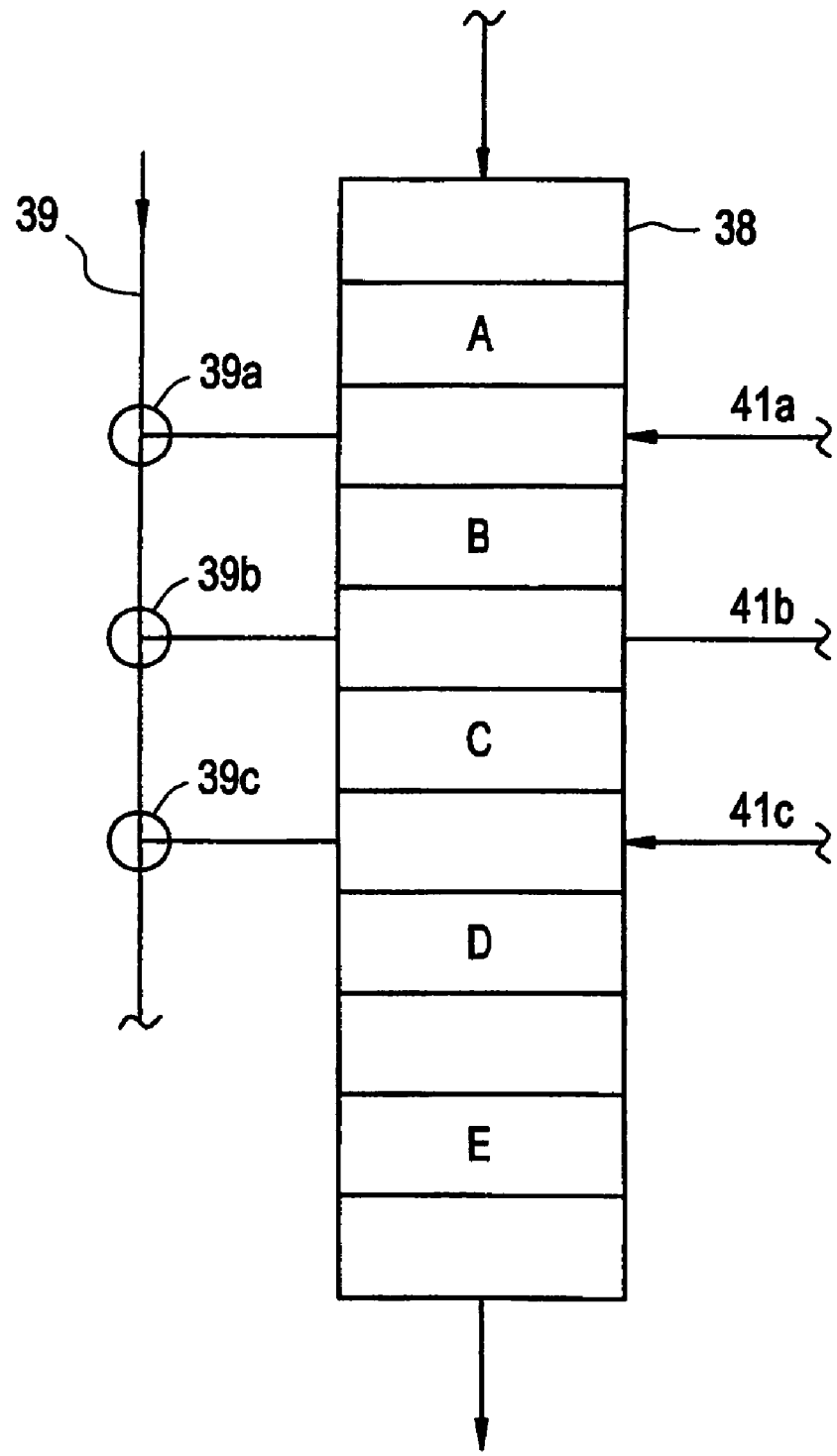
FIG. 3 is a schematic illustration of an alkylation reaction comprising a plurality of series-connected catalyst beds with the interstage injection of feed components.

A preferred reactor configuration is shown in detail in FIG. 3. As illustrated there, the reactor 38 comprises five series connected catalyst beds designated as beds A, B, C, D, and E. A benzene-ethylene feed stream is supplied to the top of the reactor and into Bed A. An ethylene feed stream is supplied via line 39 and proportionating valves 39a, 39b and 39c to provide for the appropriate interstage injection of ethylene. Benzene can also be introduced between the catalyst stages by means of secondary benzene supply lines 41a, 41b and 41c, respectively. As will be recognized, the parallel reactor 38A will be configured with similar manifolding as shown in FIG. 3 with respect to reactor 38.

Returning to FIG. 2, the effluent stream from one or both of the alkylation reactors 38 and 38A is supplied through a two-way, three-position outlet valve 44 and outlet line 45 to a two-stage benzene recovery zone which comprises as the first stage a prefractionation column 47. Column 47 is operated to provide a light overhead fraction including benzene which is supplied via line 48 to the input side of heater 34 where it is mixed with benzene in line 32 and then to the alkylation reactor input line 30. A heavier liquid fraction containing benzene, ethylbenzene and polyethylbenzene is supplied via line 50 to the second stage 52 of the benzene separation zone. Stages 47 and 52 may take the form of distillation columns of any suitable type, typically, columns having from about 20-60 trays. The overhead fraction from column 52 contains the remaining benzene, which is recycled via line 54 to the alkylation reactor input. Thus, lines 48 and 54 correspond to the output line 8 of FIG. 1. The heavier bottoms fraction from column 52 is supplied via line 56 to a secondary separation zone 58 for the recovery of ethylbenzene. The overhead fraction from column 58 comprises relatively pure ethylbenzene, which is supplied to storage or to any suitable product destination by way of line 60. By way of example, the ethylbenzene may be used as a feed stream to a styrene plant in which styrene is produced by the dehydrogenation of ethylbenzene. The bottoms fraction containing polyethylbenzenes, heavier aromatics such as cumene and butylbenzene, and normally only a small amount of ethylbenzene is supplied through line 61 to a tertiary polyethylbenzene separation zone 62. As described below, line 61 is provided with a proportioning valve 63 which can be used to divert a portion of the bottoms fraction directly to the transalkylation reactor. The bottoms fraction of column 62 comprises a residue, which can be withdrawn from the process via line 64 for further use in any suitable manner. The overhead fraction from column 62 comprises a polyalkylated aromatic component containing diethylbenzene and a smaller amount of triethylbenzene and a minor amount of ethylbenzene is supplied to an on stream transalkylation reaction zone. Similarly as described above with respect to the alkylation reactors, parallel transalkylation reactors 65 and 66 are provided through inlet and outlet manifolding involving valves 67 and 68. Both of reactors 65 and 66 can be placed on stream at the same time so that both are in service in a parallel mode of operation. Alternatively, only one transalkylation reactor can be on-stream with the other undergoing regeneration operation in order to burn coke off the catalyst beds. By minimizing the amount of ethylbenzene recovered from the bottom of column 58, the ethylbenzene content of the transalkylation feed stream can be kept small in order to drive the transalkylation reaction in the direction of ethylbenzene production. The polyethylbenzene fraction withdrawn overhead from column 62 is supplied through line 69 and mixed with benzene supplied via line 70. This mixture is then supplied to the on-line transalkylation reactor 65 via line 71. Preferably, the benzene feed supplied via line 70 is of relatively low water content, about 0.05 wt. % or less. Preferably, the water content is reduced to a level of about 0.02 wt. % or less and more preferably to less than 0.01 wt. %, 0.002 wt % or less. The transalkylation reactor is operated as described before in order to maintain the benzene and alkylated benzenes within the transalkylation reactor in the liquid phase. Typically, the transalkylation reactor may be operated to provide an average temperature within the transalkylation reactor of about 65°-290° C. and an average pressure of about 600 psi. The preferred catalyst employed in the transalkylation reactor is zeolite Y. The weight ratio of benzene to polyethylbenzene should be at least 1:1 and preferably is within the range of 1:1 to 4:1.

The output from the transalkylation reactor or reactors containing benzene, ethylbenzene, and diminished amounts of polyethylbenzene is recovered through line 72. Typically, line 72 will be connected to the inlet lines 47a for recycle to the prefractionation column 47 as shown. However, the effluent from the liquid-phase transalkylation reactor may be supplied to either or both of distillation columns 47 and 52.

Returning to the operation of the separation system, in one mode of operation the entire bottoms fraction from the ethylbenzene separation column 58 is applied to the tertiary separation column 62 with overhead fractions from this zone then applied to the transalkylation reactor. This mode of operation offers the advantage of relatively long cycle lengths of the catalyst in the transalkylation reactor between regeneration of the catalyst to increase the catalyst activity. Another mode of operation of the invention achieves this advantage by supplying a portion of the output from the ethylbenzene separation column 58 through valve 63 directly to the transalkylation reactor.

As shown in FIG. 2, a portion of the bottoms fraction from the secondary separation zone 58 bypasses column 62 and is supplied directly to the transalkylation reactor 65 via valve 63 and line 88. A second portion of the bottoms fraction from the ethylbenzene column is applied to the tertiary separation column 62 through valve 63 and line 90. The overhead fraction from column 62 is commingled with the bypass effluent in line 88 and the resulting mixture is fed to the transalkylation reactor via line 67. In this mode of operation a substantial amount of the bottoms product from column 58 can be sent directly to the transalkylation reactor, bypassing the polyethylbenzene column 62. Normally, the weight ratio of the first portion supplied via line 88 directly to the transalkylation reactor to the second portion, supplied initially via line 90 to the polyethylbenzene would be within the range of about 1:2 to about 2:1. However, the relative amounts may vary more widely to be within the range of a weight ratio of the first portion to the second portion in a ratio of about 1:3 to 3:1.

The molecular sieve catalyst employed in the alkylation reaction zone and the transalkylation reaction zone may be the same or different, but as described below, it usually will be preferred to employ different molecular sieves.

The molecular sieve catalyst employed in the critical phase alkylation reactor will normally be of a larger pore size characteristic than catalysts such as silicalite, which are employed in vapor phase alkylation processes. In this regard, the small to intermediate pore size molecular sieves, like silicalite, do not show good alkylation activity in critical phase conditions. In tests carried out respecting the invention, a silicalite molecular sieve of high silica-alumina ratio showed very little activity when employed in the ethylation of benzene under critical phase conditions. However, the same catalyst, when the reactor conditions were converted to gas phase conditions in which the benzene in the gas phase showed good alkylation activity.

While a zeolite Y catalyst can be used in the alkylation reactor, preferably, the molecular sieve catalyst employed in the critical phase alkylation reactor is a zeolite beta catalyst, which can be a conventional zeolite beta or a modified zeolite beta of the various types as described below. The zeolite beta catalyst will normally be formulated in extrudate pellets of a size of about ⅛-inch or less, employing a binder such as silica or alumina. A preferred form of binder is silica, which results in catalysts having somewhat enhanced deactivation and regeneration characteristics than zeolite beta formulated with a conventional alumina binder. Typical catalyst formulations may include about 20 wt. % binder and about 80 wt. % molecular sieve.

The catalyst employed in the transalkylation reactor normally will take the form of a zeolite Y catalyst, such as zeolite Y or ultra-stable zeolite Y. As noted above, the zeolite Y type of molecular sieve can also be employed in the critical phase alkylation reactor but normally a zeolite beta type of catalyst is employed.

Various zeolites of the Y and beta types are in themselves well known in the art. For example, zeolite Y is disclosed in U.S. Pat. No. 4,185,040 to Ward, and zeolite beta is disclosed in U.S. Pat. No. 3,308,069 to Wadlinger and U.S. Pat. No. 4,642,226 to Calvert et al.

The zeolite beta employed in the critical phase alkylation reactor can be conventional zeolite beta, or it may be modified zeolite beta of various types described in greater detail below. Preferably, a modified zeolite beta is used. The zeolite beta employed in the present invention can be a high silica/alumina ratio zeolite beta, a rare earth lanthanide modified beta, specifically lanthanum-modified zeolite beta, or a ZSM-12 modified zeolite beta as described in detail below.

Basic procedures for the preparation of zeolite beta are well known to those skilled in the art. Such procedures are disclosed in the aforementioned U.S. Pat. No. 3,308,069 to Wadlinger et al and U.S. Pat. No. 4,642,226 to Calvert et al and European Patent Publication No. 159,846 to Reuben, the disclosures of which are incorporated herein by reference. The zeolite beta can be prepared to have a low sodium content, i.e. less than 0.2 wt. % expressed as $Na_2O$ and the sodium content can be further reduced to a value of about 0.02 wt. % by an ion exchange treatment.

As disclosed in the above-referenced U.S. patents to Wadlinger et al., and Calvert et al, zeolite beta can be produced by the hydrothermal digestion of a reaction mixture comprising silica, alumina, sodium or other alkyl metal oxide, and an organic templating agent. Typical digestion conditions include temperatures ranging from slightly below the boiling point of water at atmospheric pressure to about 170° C. at pressures equal to or greater than the vapor pressure of water at the temperature involved. The reaction mixture is subjected to mild agitation for periods ranging from about one day to several months to achieve the desired degree of crystallization to form the zeolite beta. The resulting zeolite beta is normally characterized by a silica to alumina molar ratio (expressed as $SiO_2/Al_2O_3$) of between about 20 and 50.

The zeolite beta is then subjected to ion exchange with ammonium ions at uncontrolled pH. It is preferred that an aqueous solution of an inorganic ammonium salt, e.g., ammonium nitrate, be employed as the ion-exchange medium. Following the ammonium ion-exchange exchange treatment, the zeolite beta is filtered, washed and dried, and then calcined at a temperature between about 530° C. and 580° C. for a period of two or more hours.

Zeolite beta can be characterized by its crystal structure symmetry and by its x-ray diffraction patterns. Zeolite beta is a molecular sieve of medium pore size, about 5-6 angstroms, and contains 12-ring channel systems. Zeolite beta is of tetragonal symmetry $P4_122$, a=12.7, c=26.4 Å (W. M. Meier and D. H. Olson Butterworth, *Atlas of Zeolite Structure Types*, Heinemann, 1992, p. 58); ZSM-12 is generally characterized by monoclinic symmetry. The pores of zeolite beta are generally circular along the 001 plane with a diameter of about 5.5 angstroms and are elliptical along the 100 plane with diameters of about 6.5 and 7.6 angstroms. Zeolite beta is further described in Higgins et al, "The framework topology of zeolite beta," *Zeolites*, 1988, Vol. 8, November, pp. 446-452, the entire disclosure of which is incorporated herein by reference.

The zeolite beta formulation employed in carrying out the present invention may be based upon conventional zeolite beta, such as disclosed in the aforementioned patent to Calvert et al, a lanthanide series-promoted zeolite beta such as lanthanum-modified zeolite beta as disclosed in the aforementioned EP Patent Publication No. 507,761 to Shamshoum et al, or a zeolite beta modified by an intergrowth of ZSM-12 crystals as disclosed in U.S. Pat. No. 5,907,073 to Ghosh. For a further description of procedures for producing zeolite beta useful in accordance with the present invention, reference is made to the aforementioned U.S. Pat. No. 3,308,069 to Wadlinger, U.S. Pat. No. 4,642,226 to Calvert, and U.S. Pat. No. 5,907,073 to Ghosh and EPA Publication No. 507,761 to Shamshoum, the entire disclosures of which are incorporated herein by reference.

The invention can be carried out with a zeolite beta having a higher silica/alumina ratio than that normally encountered. For example, as disclosed in EPA Publication No. 186,447 to Kennedy, a calcined zeolite beta can be dealuminated by a steaming procedure in order to enhance the silica/alumina ratio of the zeolite. Thus, as disclosed in Kennedy, a calcined zeolite beta having a silica/alumina ratio of 30:1 was subjected to steam treatment at 650° C. and 100% steam for 24 hours at atmospheric pressure. The result was a catalyst having a silica/alumina ratio of about 228:1, which was then subjected to an acid washing process to produce a zeolite beta of 250:1. Various zeolite betas, such as described above, can be subject to extraction procedures in order to extract aluminum from the zeolite beta framework by extraction with nitric acid. Acid washing of the zeolite beta is carried out initially to arrive at a high silica/alumina ratio zeolite beta. This is followed by ion-exchanging lanthanum into the zeolite framework. There should be no subsequent acid washing in order to avoid removing lanthanum from the zeolite.

In experimental work carried out respecting the present invention, a number of alkylation reactor runs were carried out employing a single stage alkylation reactor. The reactor operation is a laboratory simulation of the single stage of a multistage reactor of the type illustrated in FIG. 3.

In carrying out the experimental work, six catalysts, denominated herein as Catalyst C-1 through Catalyst C-6, were used in the laboratory single stage alkylation reactor. Catalyst C-1 was a silicalite catalyst used in gas phase conditions and also in critical phase conditions. Catalyst C-1 was operated at reactor temperatures ranging from about 380° C. inlet to about 425° C. outlet, with the reactor pressure about 300 psig for gas phase conditions and about 400 psig for critical phase operation. This catalyst run was carried out for about 18 days. Throughout the course of the run, xylenes were observed in the effluent. The xylene content, based upon the ethylbenzene content of the effluent, was initially about 470 ppm and declined with time to about 400 ppm during the initial gas phase alkylation. When the pressure was increased to the supercritical stage, the xylene content increased to about 490 ppm and then declined and continued to decline to a value of about 300 after the pressure was reduced to again simulate gas phase alkylation. The benzene-ethylene mole ratio throughout the run was maintained at about 10.

The remaining catalysts employed in the experimental work were zeolite betas modified by the inclusion of lanthanum. The catalysts designated as C-2 through C-6 involved lanthanum modified beta formulated with an silica binder. For Catalyst C-2, the zeolite beta had a silica/alumina ratio of 150 with lanthanum incorporated in an amount to provide a lanthanum/aluminum atomic ratio of 1.25. Catalyst C-3 was based upon the same zeolite beta having a silica/alumina of 150, but for this catalyst the lanthanum was incorporated into the zeolite beta to provide a lanthanum/aluminum atomic ratio of 0.75. For Catalyst C-4, the zeolite beta had a silica/alumina ratio of 50 with a lanthanum/aluminum atomic ratio of 0.75. For Catalyst C-5 the zeolite beta exhibited a silica/alumina ratio of 150, but here the lanthanum/aluminum atomic ratio was 1.0. A final lanthanum beta catalyst C-6, was also formulated with a silica binder. Here, the silica/alumina ratio of the zeolite was 150, and the lanthanum-aluminum atomic ratio was 1.

In each of the tests carried employing Catalyst C-2 through Catalyst C-6, the alkylation reactor was operated under critical phase conditions. Generally, the temperature at the inlet side of the reactor was about 310° C.±10° C., and the outlet temperature of the reactor was about 340°-350° C.±10° C. The pressure on the reactor was maintained at a level of about 600 psig with a pressure gradient of a few psi from the inlet to the outlet side of the reactor. For Catalyst C-6 the reactor temperature was about 320° C. at the inlet and about the same or slightly higher at the outlet. In other words, there was very little temperature gradient across the reactor.

The results of the experimental work carried out with Catalyst C-2 through C-6 are illustrated in FIGS. 4-8. Turning first to FIG. 4A, the percent of the catalyst bed used in the catalytic reaction is plotted on the ordinate versus the days on stream on the abscissa. This value was calculated based upon the maximum temperature sensed across the bed. As can be seen from an examination of FIG. 4A, the bed utilization reached 90% at Day 16 and the run continued until Day 21. At this point, the catalyst was regenerated, and at Day 22 after regeneration the bed usage dropped to about 50% and then began to increase throughout the remainder of the run. FIG. 4B shows the percent of ethylbenzene plotted on the ordinate versus the time on stream in days on the abscissa. FIG. 4C illustrates the by-product yields, BP, relative to ethylbenzene equivalents in parts per million plotted on the ordinate for propylbenzenes, butylbenzenes, and heavy components, principally long chain alkyl aromatics.

Figure 4A:
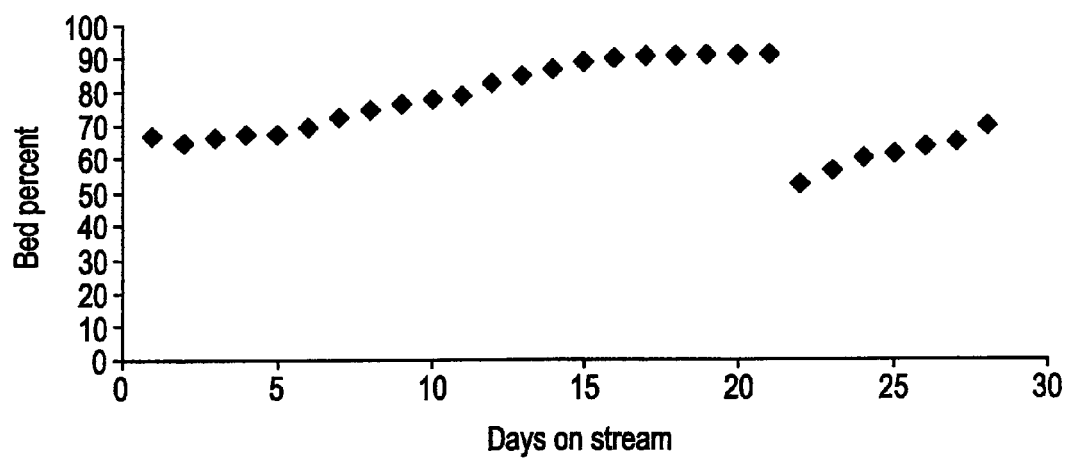
FIGS. 4A, 4B, 4C, and 4D illustrate the results of experimental work carried out with a lanthanum-modified zeolite beta alkylation catalyst.
Figure 4B:
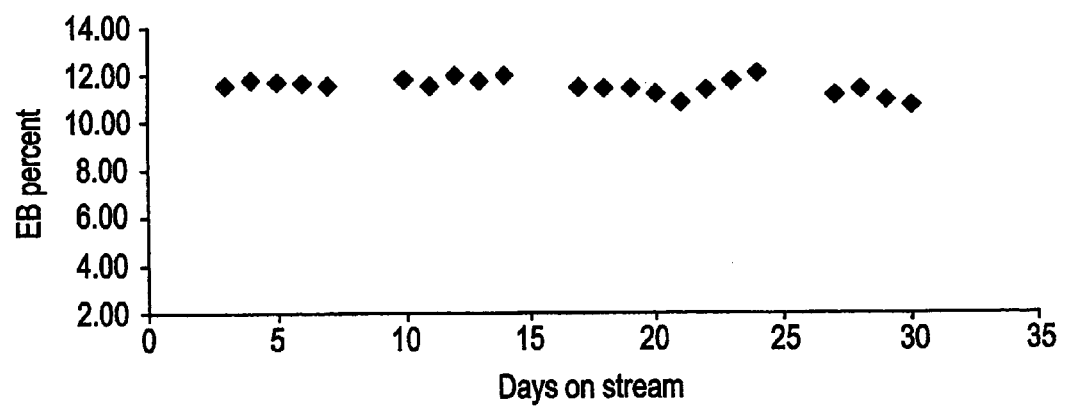
Figure 4C:
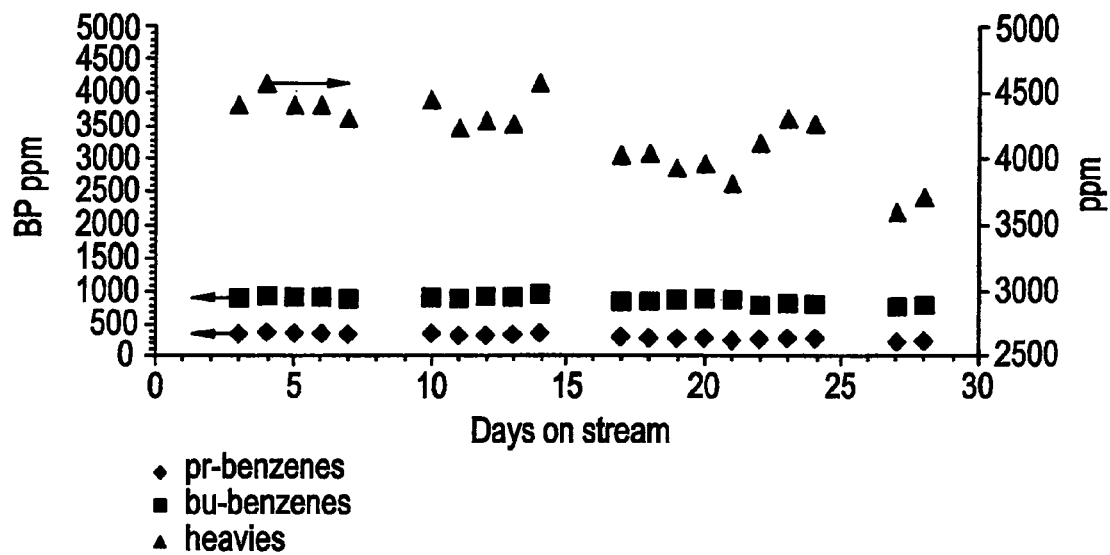
Figure 4D:
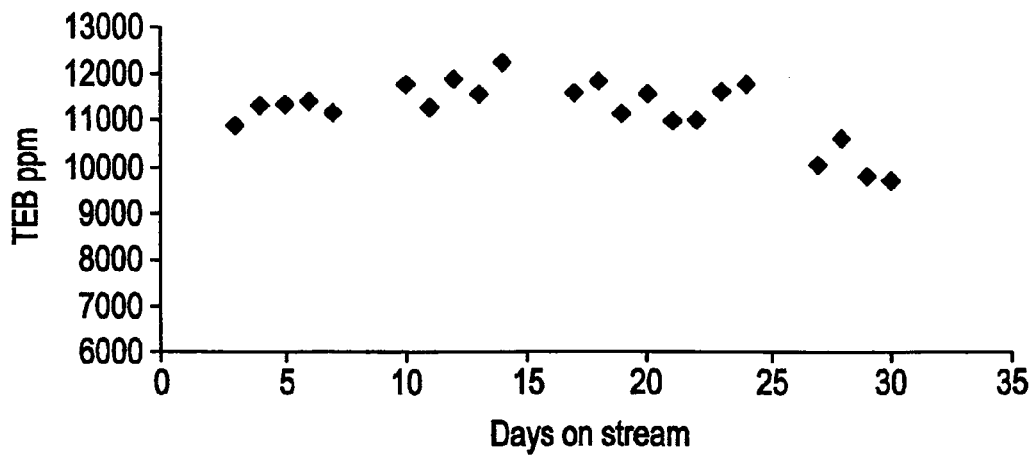
Figure 5A:
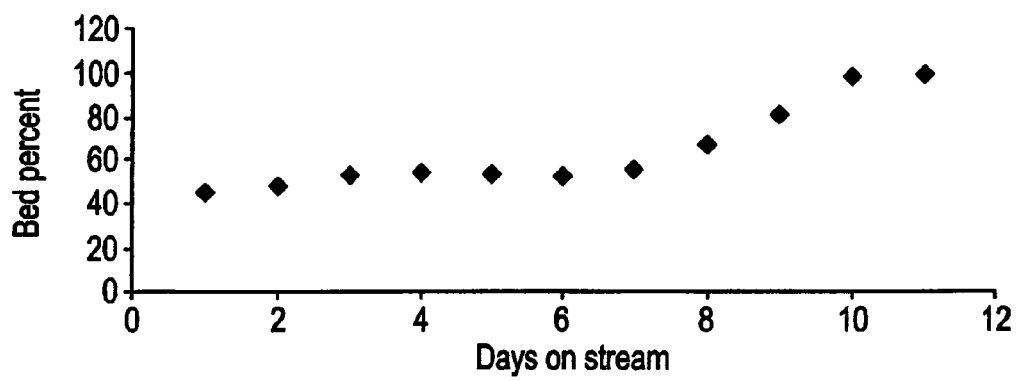
FIGS. 5A and 5B show the results of experimental work carried out with another lanthanum beta alkylation catalyst of reduced lanthanum content.
Figure 5B:
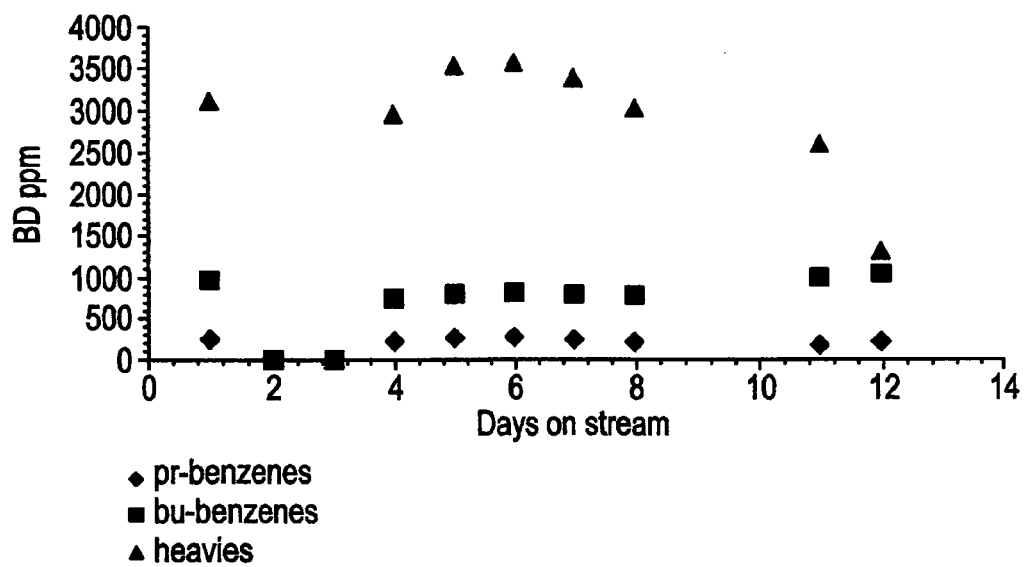
Figure 6A:
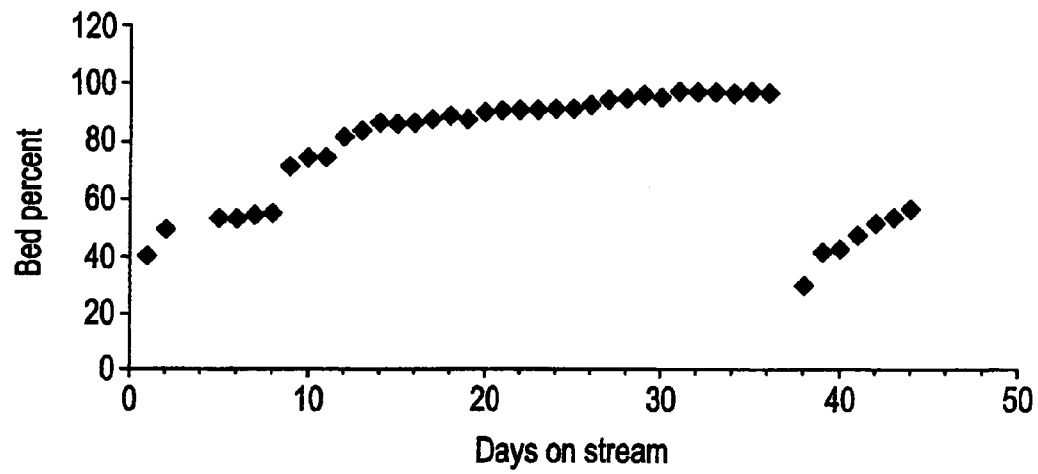
FIGS. 6A, 6B, 6C, and 6D are graphs illustrating the results of experimental work carried out with yet another lanthanum-modified zeolite beta alkylation catalyst of lower silica-alumina ratio than the previous catalyst.
Figure 6B:
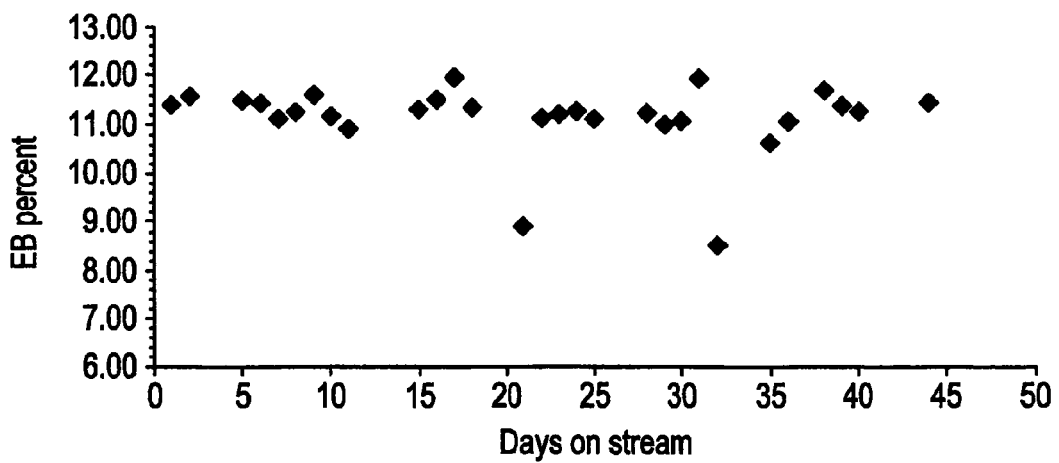
Figure 6C:
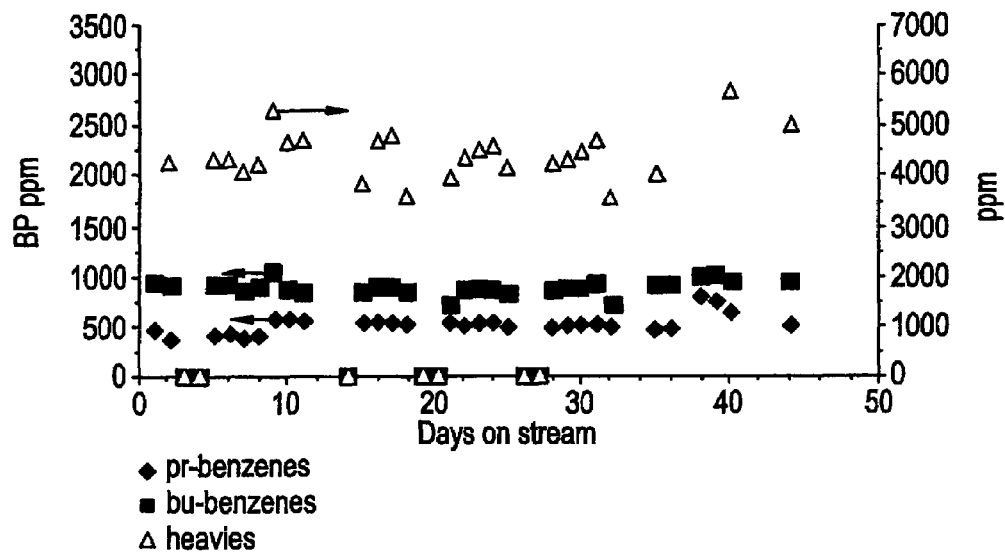
Figure 6D:
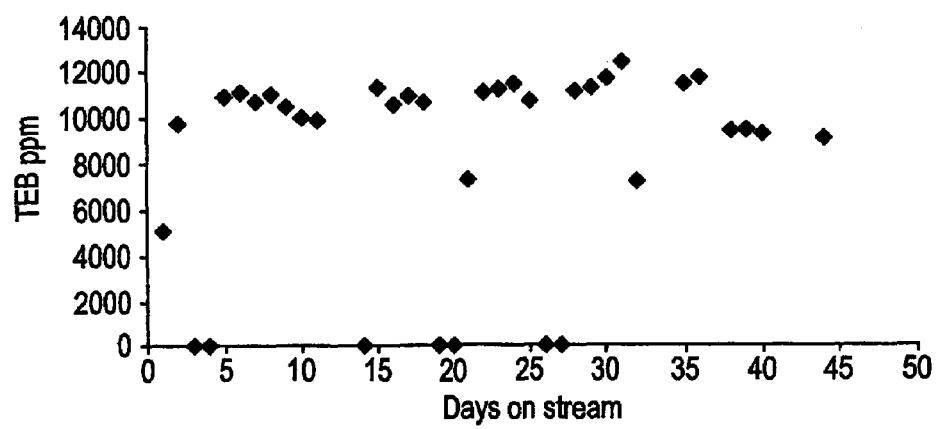

FIG. 4D illustrates the triethylbenzene (TEB) yield in parts per million plotted on the ordinate versus the time on stream in days plotted on the abscissa. Similar graphical presentations, employing the suffixes described above with respect to FIG. 4, are shown in FIGS. 5 through 8 for Catalysts C-3 through C-6, respectively, Thus, for Catalyst C-3 the percent of the bed used is plotted on the ordinate in FIG. 5A versus the time on stream on the abscissa. FIG. 5C illustrates the by-product yields relative to ethylbenzene for propylenebenzenes, butylbenzenes, and the heavy aromatic content of the effluent. It will be noted that Catalyst C-3 appeared to deactivate relatively rapidly reaching the 100% bed usage point at Day 10.

FIGS. 6A, 6B, 6C, and 6D illustrate, respectively, the percent bed used, the ethylbenzene equivalent yield, the by-products of propylbenzenes, butylbenzenes, and heavies, and the TEB yield observed for Catalyst C-4. The run was shut down briefly at Day 8 and then continued, at which point the bed usage increased from less than 60% to more than 70% upon start up. The continued run reached near 100% bed usage at Day 31 and was continued for an additional five (5) days at which point the catalyst was regenerated and the run reinstituted at Day 38.

Figure 7A:
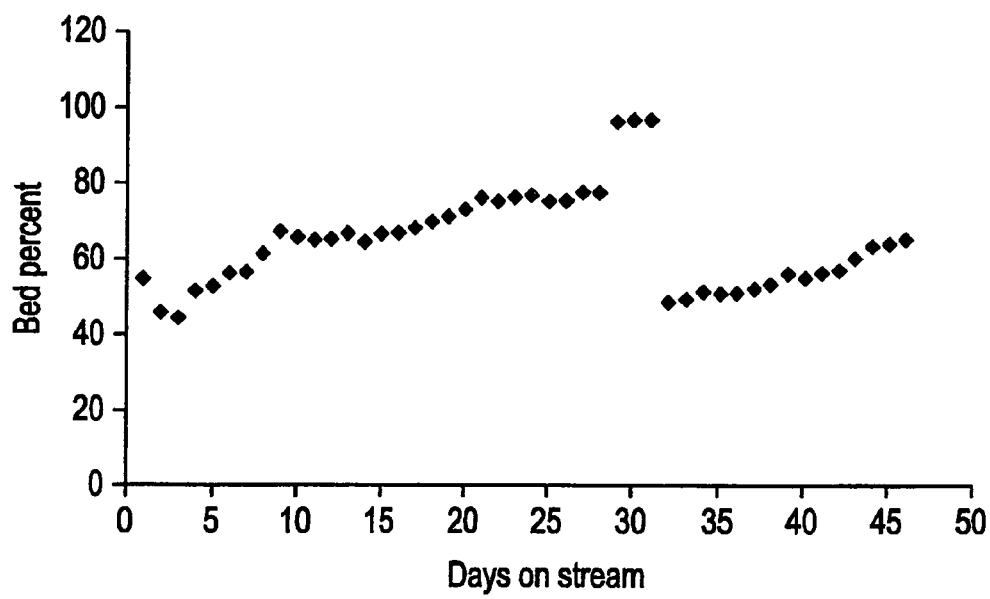
FIGS. 7A, 7B, 7C, and 7D are graphs illustrating the results of experimental work carried out with yet another zeolite beta alkylation catalyst of intermediate lanthanum content.
Figure 7B:
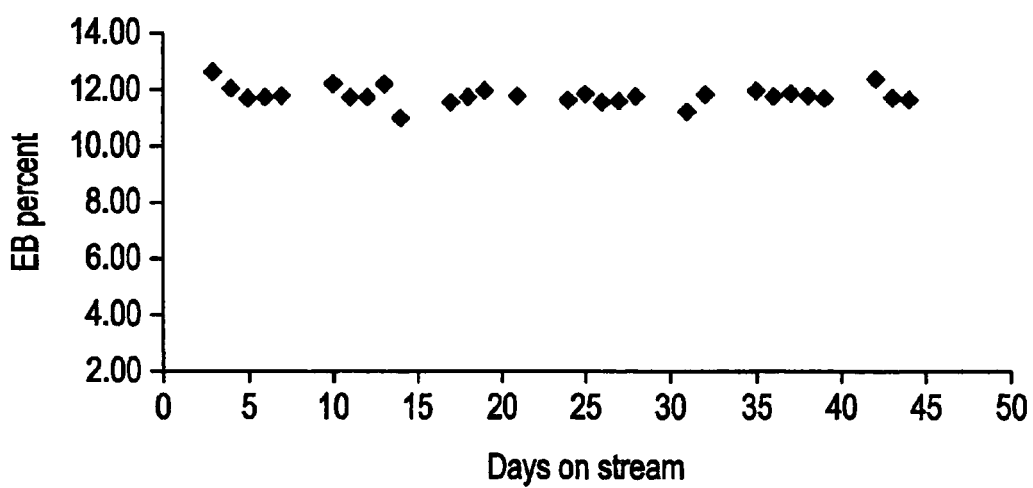
Figure 7C:
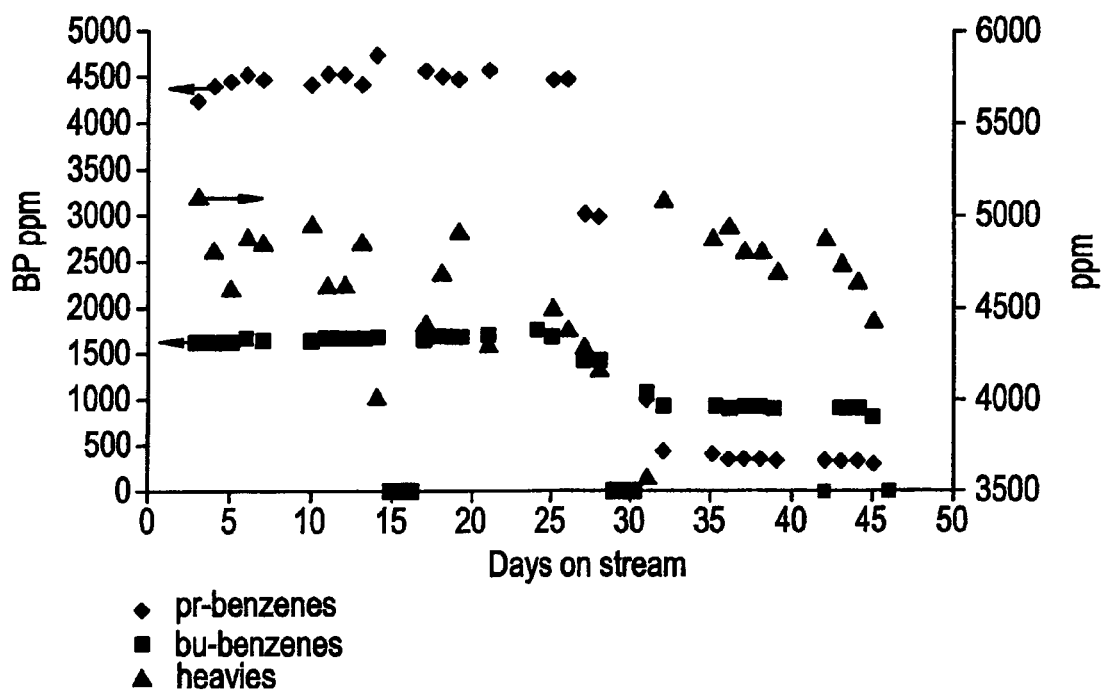
Figure 7D:
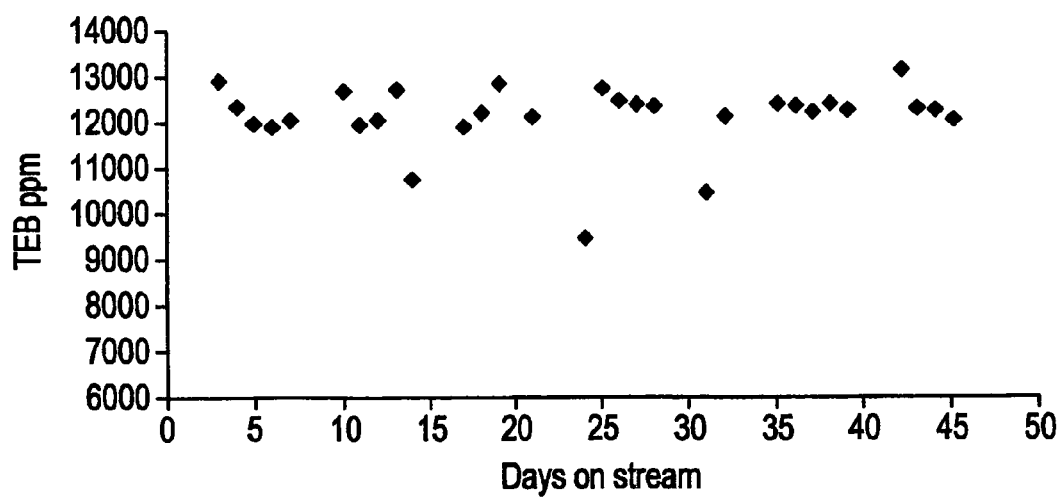

FIGS. 7A through 7D show these same values for Catalyst C-5. As shown in FIG. 7A, bed usage reached about 80% at Day 21 and continued at this level until Day 28, at which point temperature measurements indicated that the bed usage increased sharply to near 100%. After additional operation for three days, the catalyst was regenerated and the run reinstituted at Day 32 catalyst bed.

Figure 8A:
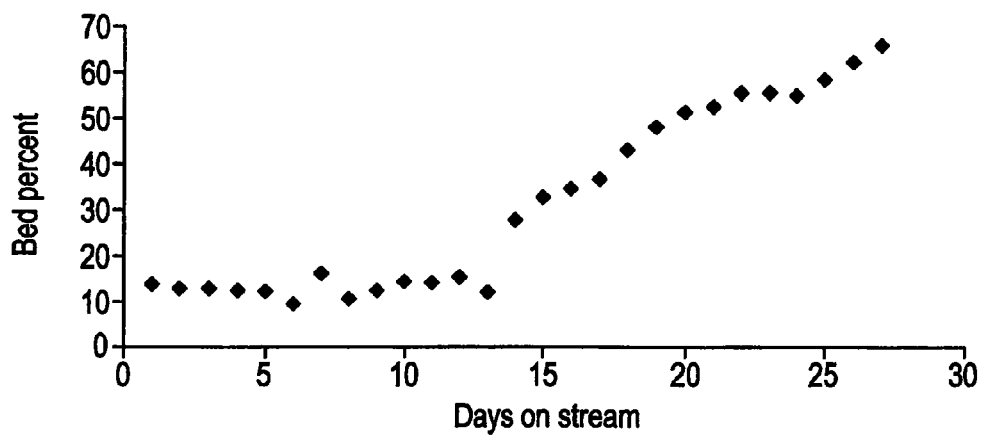
FIGS. 8A, 8B, 8C, and 8D are graphs illustrating the results of experimental work carried out with another lanthanum-modified zeolite beta.
Figure 8B:
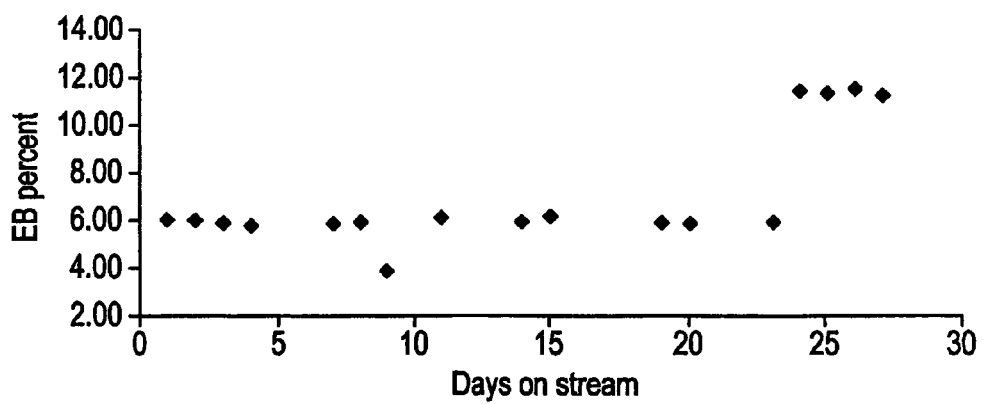
Figure 8C:
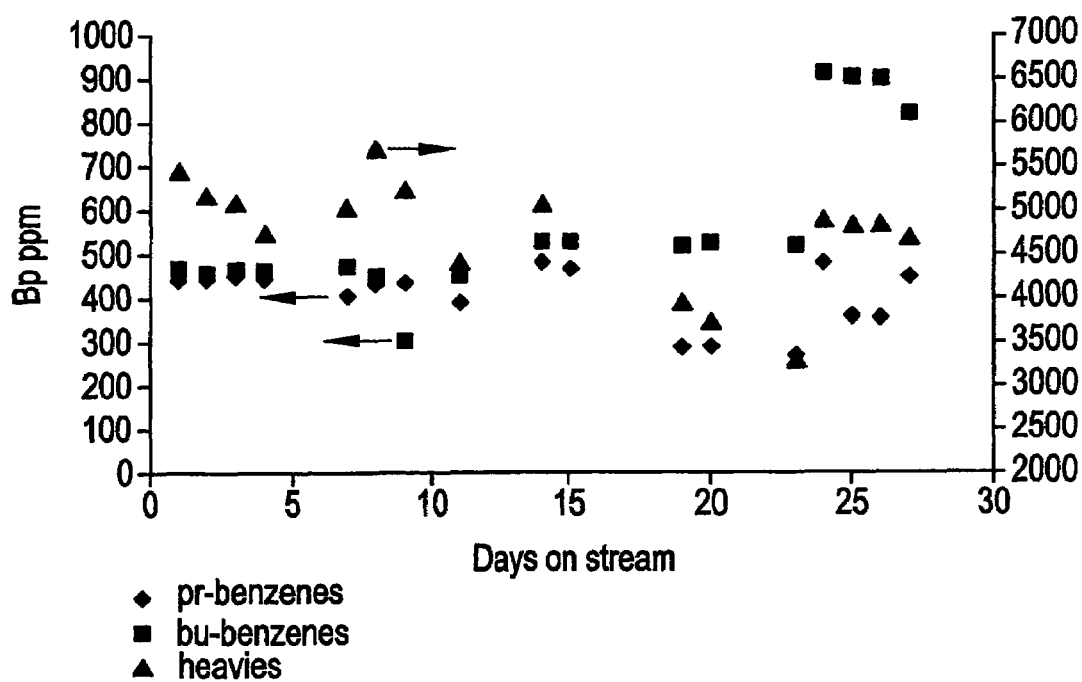
Figure 8D:
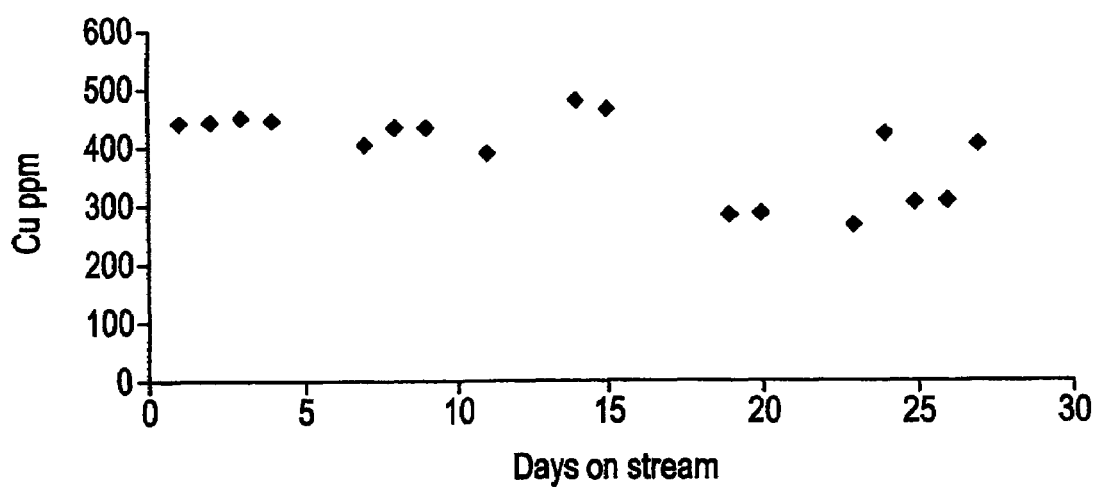

FIGS. 8A through 8C show the results observed for Catalyst C-6 for bed usage, EB production, and by-product yields (BP), respectively. FIG. 8D shows the cumene yield, CU, based on EB equivalents in parts per million versus the days on stream. In contrast to the runs carried out with Catalyst C-2 through C-5, which employed a benzene-ethylene ratio of 10:1, the run employing catalyst C-6 was initially carried out at an ethylenelbenzene mole ratio of 20:1. At Day 24, during this initial period the ethylbenzene EB production was at about 6%. When the ethylene feed stream was doubled to reduce the benzene-ethylene mole ratio to 10:1, the EB production approximately doubled since the ethylene was the limiting factor. The bed usage was at less than 70% after 28 days on stream, with the ethylbenzene production remaining relatively constant.

From an examination of the data presented in FIGS. 4 through 7 for the alumina-bound Catalyst C-2 through C-5, it can be seen that promotion of the zeolite beta with the rare earth metal lanthanum materially increased the aging quality of the catalyst. Good aging qualities were shown for Catalyst C-2, C-4, and C-5. These qualities were observed at lanthanum-aluminum atomic ratios ranging from 0.75 to 1.25 except in the case of Catalyst C-3, which was a high silicon-aluminum ratio catalyst with a relatively low lanthanum-aluminum value of 0.75. Here, the amount of lanthanum, in terms of lanthanum content of the zeolite beta without regard to the silicon-aluminum ratio, was lower than for the other catalysts. As indicated, this catalyst deactivated rapidly.

Having described specific embodiments of the present invention, it will be understood that modifications thereof may be suggested to those skilled in the art, and it is intended to cover all such modifications as fall within the scope of the appended claims.

What is claimed:

1. A process for the production of ethylbenzene comprising:
   (a) supplying an aromatic feedstock having a benzene content of at least 95 wt. % into an alkylation reaction zone and into contact with a zeolite beta alkylation catalyst having a crystalline structure and a silica/alumina ratio within the range of 20-500; wherein said zeolite beta comprises a lanthanum-modified zeolite beta having a lanthanum content of 0.25-5 wt. %
   (b) supplying ethylene to said reaction zone in an amount to provide a benzene/ethylene mole ratio within the range of 1-15;
   (c) operating said alkylation reaction zone at temperature and pressure conditions in which benzene is in the supercritical phase to cause ethylation of said benzene in the presence of said alkylation catalyst to produce an alkylation product containing benzene, ethylbenzene, and polyalkylated aromatic by-products;
   (d) recovering said alkylation product from said reaction zone and supplying said product to a recovery zone for the separation and recovery of ethylbenzene from the alkylated product and the separation and recovery of a polyalkylated aromatic component including diethylbenzene;
   (e) supplying at least a portion of the polyalkylated aromatic component including diethylbenzene to a transalkylation reactor and supplying benzene to the transalkylation reactor; and
   (f) using a zeolite-Y catalyst in the transalkylation reactor and operating the transalkylation reactor under temperature and pressure conditions effective to maintain the benzene and the polyalkylated aromatics in liquid phase conditions to cause disproportionation of the polyalkylated aromatics to produce a disproportionation product having a reduced diethylbenzene and an enhanced ethylbenzene content.

2. The process of claim 1 wherein the benzene/ethylene mole ratio is less than 10.

3. The process of claim 1 wherein the benzene/ethylene mole ratio is within the range of 3-8.

4. The process of claim 1 wherein the benzene to ethylene mole ratio is less than 10.

5. The process of claim 1 wherein said zeolite beta has a lanthanum/aluminum atomic ratio within the range of 0.75-1.25.

6. The process of claim 1 wherein said zeolite beta has a silica/alumina ratio within the range of 50-150.

7. The process of claim 1, wherein the alkylation product contains ethylbenzene as a primary product and polyalkylated by-products of no more than 60 wt. % of the ethylbenzene.

8. The process of claim 1 wherein the alkylation reactor comprises a plurality of catalyst beds connected in series.

9. The process of claim 8 wherein each bed of said plurality of catalyst beds contains a molecular sieve catalyst.

10. The process of claim 9 further comprising the step of using a zeolite-Y catalyst in the catalyst beds of the alkylation zone.

11. The process of claim 8 further comprising the steps of:
    using two or more alkylation reactors in a parallel mode of operation in which they are all in service at the same time;
    periodically taking at least one reactor off-stream for regeneration of the catalyst; and
    keeping at least one of the alkylation reactor in service while another reactor is off-stream.

12. The process of claim 8, further comprising the step of injecting of ethylene and benzene between stages in the alkylation reactor, wherein said injecting causes additional ethylbenzene production.

13. The process of claim 8, further comprising the step of injecting of ethylene and benzene between stages in the alkylation reactor, wherein said injecting promotes transalkylation within the alkylation reactor in which benzene and diethylbenzene react through a disproportionation reaction to produce ethylbenzene.

14. The process of claim 1, wherein the polyalkylbenzene by-products produced during alkylation have a reduced xylene content.

15. The process of claim 1, wherein the alkylation catalyst has a silica/alumina ratio of from greater than 50 to 500.

16. A process for the production of ethylbenzene comprising:
    (a) providing an alkylation reaction zone containing an zeolite beta alkylation catalyst having a crystalline structure and a silica/alumina ratio within the range of 20-500; wherein said zeolite beta comprises a lanthanum-modified zeolite beta having a lanthanum content of 0.25-5 wt. %
    (b) supplying a feedstock containing benzene in an amount of at least 95% of the aromatic content and supplying ethylene to said reaction zone in an amount to provide a benzene/ethylene mole ratio within the range of 1-15;
    (c) operating said alkylation reaction zone at temperature and pressure conditions in which benzene is in the supercritical phase to cause ethylation of said benzene in the presence of said alkylation catalyst to produce an alkylation product comprising a mixture of benzene, ethylbenzene, and polyethyl benzenes;
    (d) recovering the alkylation product from said alkylation reaction zone and supplying said product from said alkylation reaction zone to a recovery zone for the separation and recovery of ethylbenzene from the alkylated product and the separation and recovery of a polyalkylated aromatic component including diethylbenzene;
    (e) supplying at least a portion of the polyalkylated aromatic component including diethylbenzene in said polyalkylated aromatic component to a transalkylation reaction zone containing a zeolite-Y transalkylation catalyst:
    (f) supplying benzene to said transalkylation reaction zone; and (g) operating said transalkylation reaction zone under temperature and pressure conditions effective to maintain the polyalkylated aromatic component supplied to said transalkylation zone to cause disproportionation of said polyalkylated aromatic fraction to produce a disproportionation product having a reduced diethylbenzene content and an enhanced ethylbenzene content.

17. The process of claim 16 wherein said transalkylation reaction zone is operated under temperature and pressure conditions effective to maintain the polyalkylated aromatic component supplied to said transalkylation zone in the liquid phase.

18. The method process of claim 16 wherein said zeolite beta alkylation catalyst is a rare earth metal modified zeolite beta catalyst.

19. The process of claim 16, wherein the alkylation product contains ethylbenzene as a primary product and heavier alkylated by-products of no more than 60 wt. % of the ethylbenzene.

20. The process of claim 16, wherein the alkylation products produced during alkylation have a reduced xylene content.

21. The process of claim 16, wherein the alkylation catalyst has a silica/alumina ratio of from greater than 50 to 500.

* * * * *